United States Patent
Shanker (10) Patent No.: US 11,833,368 B2
(45) Date of Patent: Dec. 5, 2023

(54) SYSTEMS AND METHODS FOR DELIVERING LOW-LEVEL ELECTROMAGNETIC RADIATION TO A PATIENT

(71) Applicant: Jonathan A. Shanker, Clayton, MO (US)

(72) Inventor: Jonathan A. Shanker, Clayton, MO (US)

(73) Assignee: Jonathan A. Shanker, Clayton, MO (US)

( * ) Notice: Subject to any disclaimer, the term of this patent is extended or adjusted under 35 U.S.C. 154(b) by 100 days.

(21) Appl. No.: 17/185,103

(22) Filed: Feb. 25, 2021

(65) Prior Publication Data

US 2021/0244967 A1 Aug. 12, 2021

Related U.S. Application Data (63) Continuation of application No. 29/788,005, filed on Feb. 8, 2021, and a continuation-in-part of application
(Continued)

(51) Int. Cl.
*A61N 5/06* (2006.01)

(52) U.S. Cl.
CPC .... *A61N 5/0625* (2013.01); *A61N 2005/0626* (2013.01); *A61N 2005/0632* (2013.01);
(Continued)

(58) Field of Classification Search
CPC ............ A61N 1/40; A61N 5/0625; A61N 2005/0626; A61N 2005/0632;
(Continued)

(56) References Cited

U.S. PATENT DOCUMENTS

| 4,836,778 A | 6/1989 | Baumrind et al. |
| 5,163,194 A * | 11/1992 | Dixon ............... A47G 9/1081 5/639 |

(Continued)

FOREIGN PATENT DOCUMENTS

| CN | 209734485 U | 12/2019 |
| EP | 2110159 B1 | 1/2013 |

(Continued)

OTHER PUBLICATIONS

Foley, Kevin T., et al., Randomized, prospective, and controlled clinical trial of pulsed eletromagnetic field stimulation for cervical fusion, The Spine Journal, 2008, pp. 436-442, No. 8, Elsevier Inc.
(Continued)

*Primary Examiner* — Mallika D Fairchild
*Assistant Examiner* — Shreya Anjaria
(74) *Attorney, Agent, or Firm* — Armstrong Teasdale LLP (57) ABSTRACT

A device for delivering low-level electromagnetic radiation to a patient includes a core portion including an upper surface and defining at least a portion of a base surface opposite the upper surface. The base surface is substantially planar and configured to rest on a substrate. The device also includes a cushion layer mounted on the upper surface and substantially defining a contact surface. The contact surface is opposite the base surface and contoured to support a curvature of a sub-occipital region and a lower neck region of the patient in a supine position. The device further includes a plurality of emitters coupled proximate to the contact surface and configured to emit low-level electromagnetic radiation transdermally to at least one of the sub-occipital region and the lower neck region.

18 Claims, 10 Drawing Sheets

Related U.S. Application Data

No. 16/787,497, filed on Feb. 11, 2020, now abandoned.

(52) U.S. Cl.
CPC ............... *A61N 2005/0643* (2013.01); *A61N 2005/0652* (2013.01); *A61N 2005/0659* (2013.01)

(58) Field of Classification Search
CPC .... A61N 2005/0643; A61N 2005/0652; A61N 2005/0659
See application file for complete search history.

(56) References Cited

U.S. PATENT DOCUMENTS

| | | | |
|---|---|---|---|
| 5,501,646 | A | 3/1996 | Miller |
| 6,016,807 | A | 1/2000 | Lodge |
| 7,347,834 | B2 * | 3/2008 | Han .................... A61F 5/04 602/32 |
| 8,874,227 | B2 | 10/2014 | Simon et al. |
| 9,004,917 | B2 | 4/2015 | Brunner et al. |
| 9,242,118 | B2 | 1/2016 | Brawn |
| 2005/0278003 | A1 | 12/2005 | Feldman |
| 2007/0248930 | A1 | 10/2007 | Brawn |
| 2012/0148976 | A1 | 6/2012 | Brawn |
| 2014/0277298 | A1 * | 9/2014 | Tapper ................ A61N 5/0616 607/91 |
| 2017/0128307 | A1 * | 5/2017 | Kim ...................... A61H 7/001 |
| 2017/0216617 | A1 * | 8/2017 | Kariguddaiah ....... A61F 5/0118 |
| 2018/0042409 | A1 | 2/2018 | Johnson |
| 2018/0063612 | A1 * | 3/2018 | Fuchs ................... H04R 1/028 |
| 2019/0083809 | A1 | 3/2019 | Zhang |
| 2019/0143114 | A1 | 5/2019 | Nelson |
| 2019/0366115 | A1 | 12/2019 | Castel |

FOREIGN PATENT DOCUMENTS

| | | | | |
|---|---|---|---|---|
| WO | 2006059889 | A1 | 6/2006 | |
| WO | WO-2006059889 | A1 * | 6/2006 | ............ A47G 9/007 |
| WO | 2019173167 | A1 | 9/2019 | |
| WO | WO-2021091038 | A1 * | 5/2021 | |

OTHER PUBLICATIONS

International Search Report and Written Opinion, dated Jul. 23, 2021, for related International Application No. PCT/US2021/017205 (15 pgs.).

Larkin-Kaiser et al., "Near-Infrared Light Therapy to Attenuate Strength Loss After Strenuous Resistance Exercise," NATA Journals, 2015, vol. 50, No. 1, retrieved from https://ncbi.nlm.nih.gov/pmc/articles/PMC4299734/ on Feb. 7, 2020, pp. 45-50.

* cited by examiner

SYSTEMS AND METHODS FOR DELIVERING LOW-LEVEL ELECTROMAGNETIC RADIATION TO A PATIENT

CROSS REFERENCE TO RELATED APPLICATIONS

This application is a continuation-in-part of, and claims priority to, U.S. application Ser. No. 16/787,497, filed Feb. 11, 2020, entitled "SYSTEMS AND METHODS FOR DELIVERING LOW-LEVEL ELECTROMAGNETIC RADIATION TO A PATIENT," the entire contents of which are hereby incorporated by reference in their entirety. This application also is a continuation of, and claims priority to, United States Design application Serial No. 29/788,005, filed Feb. 8, 2021, entitled "NECK THERAPY CUSHION," the entire contents of which are hereby incorporated by reference in their entirety.

BACKGROUND

The subject matter described herein relates generally to medical devices and, more particularly, to devices and methods for treatment of tension headaches and/or temporomandibular joint disorder (TMD) by positioning a patient to induce target treatment areas into a receptive state for receiving therapeutic amounts of electromagnetic therapy, and delivering therapeutic amounts of electromagnetic therapy to the treatment areas of the patient so positioned.

At least some known tension headaches are caused by muscle contractions in the head and neck regions. Any number of internal and environmental stressors are known to cause tension headaches, and the pain may range from mild to moderate to severe. The temporomandibular joint (TMJ) acts as a sliding hinge that connects the jawbone to the skull. Patients with TMJ disorders (commonly known as TMD) frequently exhibit symptoms of pain and limited mobility in the jaw joint as well as in the surrounding muscles and tissues. Many TMD patients suffer from other conditions and symptoms associated with TMD, including tension headaches.

At least some known devices, such as contoured pillows and oral inserts, are configured to reduce the discomfort of tension headaches and/or TMD by physically positioning the patient in a fashion that relaxes the associated muscle groups and other tissues. However, the relief afforded by such known devices is often temporary, and the devices are not generally capable of healing the affected muscles and other tissues.

Alternatively, at least some known devices are configured to reduce the discomfort of tension headaches and/or TMD by administering low dosages of electromagnetic radiation (e.g., near-infrared light) to the affected muscles and other tissues transdermally through the face, neck, or scalp. For example, the low-level electromagnetic radiation (often referred to as "low-level light therapy") is applied by emitters positioned on a skull cap, face wrap, or handheld device. However, such devices are known to produce inconsistent results, both among different patients and across different treatment sessions by a single patient.

Accordingly, a device that reduces the discomfort of tension headaches and/or TMD, promotes healing of the underlying muscles and other tissue, and is capable of producing consistent results both among different patients and across treatment sessions for a given patient would find utility.

BRIEF SUMMARY

In one aspect, a device for delivering low-level electromagnetic radiation to a patient is provided herein. The device includes a core portion including an upper surface and defining at least a portion of a base surface opposite the upper surface. The base surface is substantially planar and configured to rest on a substrate. The device also includes a cushion layer mounted on the upper surface and substantially defining a contact surface. The contact surface is opposite the base surface and contoured to support a curvature of a sub-occipital region and a lower neck region of the patient in a supine position. The device further includes a plurality of emitters coupled proximate to the contact surface and configured to emit low-level electromagnetic radiation transdermally to at least one of the sub-occipital region and the lower neck region.

The features, functions, and advantages described herein may be achieved independently in various embodiments of the present disclosure or may be combined in yet other embodiments, further details of which may be seen with reference to the following description and drawings.

DETAILED DESCRIPTION

The devices and methods described herein position a patient to induce muscles and other tissues associated with tension headaches and/or TMD into a specifically receptive state for receiving therapeutic low-level amounts of electromagnetic radiation, and also deliver therapeutic amounts of low-level electromagnetic radiation to the treatment areas of the patient so positioned. More specifically, such therapeutic low-level electromagnetic radiation, for example near infrared ("NIR") light, has been found to more effectively and consistently promote healing of muscle tissue, such as in the context of therapy for sports-related injuries, when the targeted muscle fibers are in a gently stretched state, rather than constricted or completely relaxed. The devices and methods described herein position the patient in a fashion that induces muscle fibers in the patient's head and neck into this gently stretched yet unforced receptive state, and simultaneously orient emitters to apply low-level light therapy transdermally to the muscles and other tissues that have been induced into the receptive state, thereby not only reliably and consistently alleviating pain associated with tension headaches and/or temporomandibular joint disorders (TMD), but also facilitating healing of the targeted muscles and other tissues to reduce or eliminate the incidence of tension headaches and/or TMD. Without wishing to be limited to a particular theory, low-level light therapy is believed to affect a biological change in tissue by inducing a photochemical reaction in the cell, a process referred to as photobiomodulation. For example, low-level light therapy increases the temperature in the muscles and tissues of a treatment area, and improves blood circulation to the treatment area.

The devices and methods described herein include a support having a contact surface contoured to support the curvature of the patient's sub-occipital region and adjacent lower neck region (i.e., the back of the neck below the sub-occipital region) when the patient lies in a supine position. More specifically, the support is configured to cantilever an upper portion of the patient's head beyond the edge of the support, such that the weight of the head gently stretches the patient's sub-occipital muscles, as well as surrounding tissues and muscle groups in the lower neck and head, into the light therapy-receptive state described above. The devices and methods further include emitters coupled to (e.g., embedded in) the support proximate to the contact surface and oriented to emit low-level electromagnetic radiation (e.g., NIR light) transdermally into the targeted muscle groups while they are in the receptive state.

In some embodiments, the support includes first and second support elements that are movable relative to each other to adjust a length of the support in a direction generally parallel to the patient's spine. More specifically, the first and second elements are movable relative to each other to adjust a spacing between a first portion of the contact surface, supporting the sub-occipital region, and a second portion of the contact surface, supporting the lower neck. Accordingly, the device is easily adjustable to each specific patient's neck length in order to achieve the desired receptive state of the target muscle groups and/or the desired alignment of the emitters and the target muscle groups.

In certain embodiments, the device further includes at least one side arm assembly coupled to the support, such as two side arm assemblies on opposing sides of the support. The side arm assembly includes a support arm extending from a first end to a second end, and support pads coupled to the second end. The side arm assembly also includes emitters coupled to an inner face (e.g., an inner surface) of each support pad. The emitters are positioned to emit low-level electromagnetic radiation (e.g., NIR light) transdermally into muscle groups surrounding the jaw and temple region of the patient's face, that is, muscle groups typically implicated in TMD. In particular, it has been discovered that the support, sized and contoured to induce the sub-occipital muscles and surrounding tissues into the light therapy-receptive state described above, advantageously further tends to induce the light therapy-receptive state in the muscle groups associated with TMD. A position of each support pad relative to the support arm is adjustable to align the additional emitters with these TMD-specific muscle groups and other tissues while they are in the receptive state induced by use of the support.

As used herein, an element or step recited in the singular and preceded with the word "a" or "an" should be understood as not excluding plural said elements or steps, unless such exclusion is explicitly stated. Further, references to an "embodiment" or an "implementation" are not intended to be interpreted as excluding the existence of additional embodiments or implementations that also incorporate the recited features. Moreover, unless explicitly stated to the contrary, embodiments or implementations "comprising," "including," or "having" an element or a plurality of elements having a particular property may include additional such elements not having that property.

Unless otherwise indicated, approximating language, such as "generally," "substantially," and "about," as used herein indicates that the term so modified may apply to only an approximate degree, as would be recognized by one of ordinary skill in the art, rather than to an absolute or perfect degree. Accordingly, a value modified by a term or terms such as "about," "approximately," and "substantially" is not to be limited to the precise value specified. In at least some instances, the approximating language may correspond to the precision of an instrument for measuring the value. Additionally, unless otherwise indicated, the terms "first," "second," etc. are used herein merely as labels, and are not intended to impose ordinal, positional, or hierarchical requirements on the items to which these terms refer. Moreover, reference to, for example, a "second" item does not require or preclude the existence of, for example, a "first" or lower-numbered item or a "third" or higher-numbered item.

Figure 1:
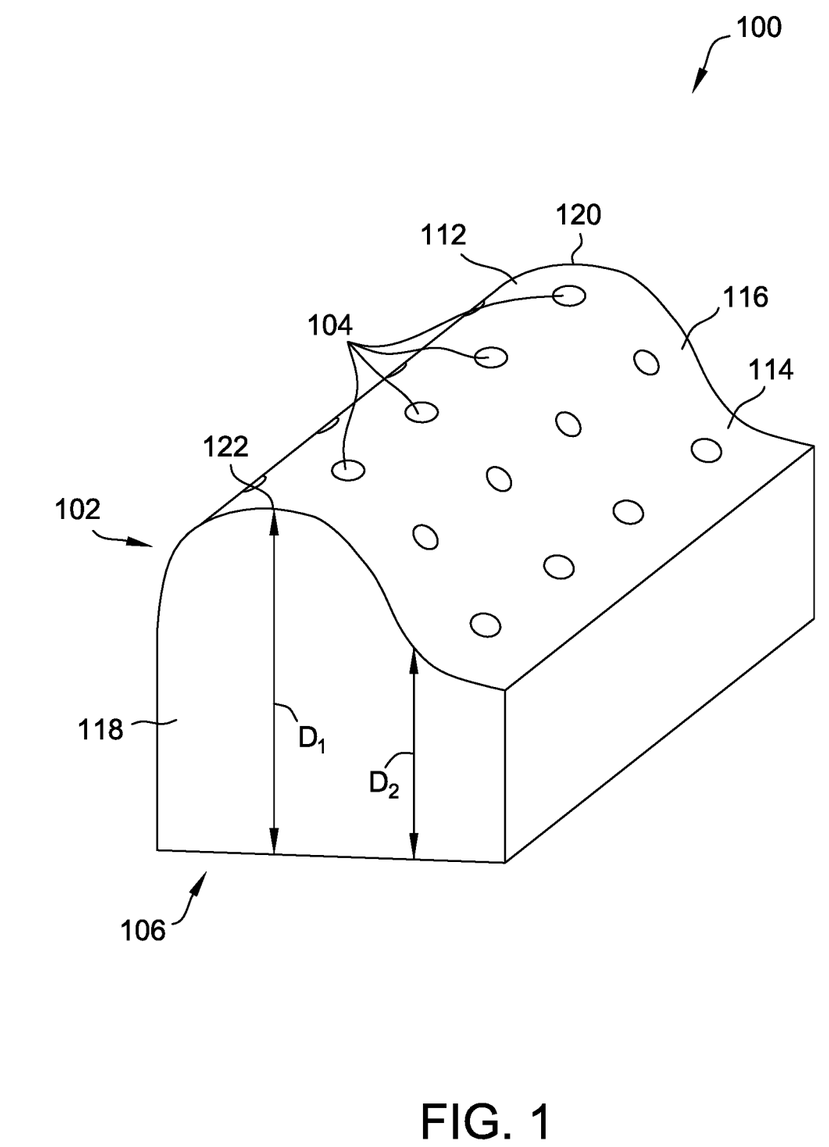
FIG. 1 is a schematic perspective view of an exemplary device for delivering low-level electromagnetic radiation to one or more treatment areas of a patient.
Figure 2:
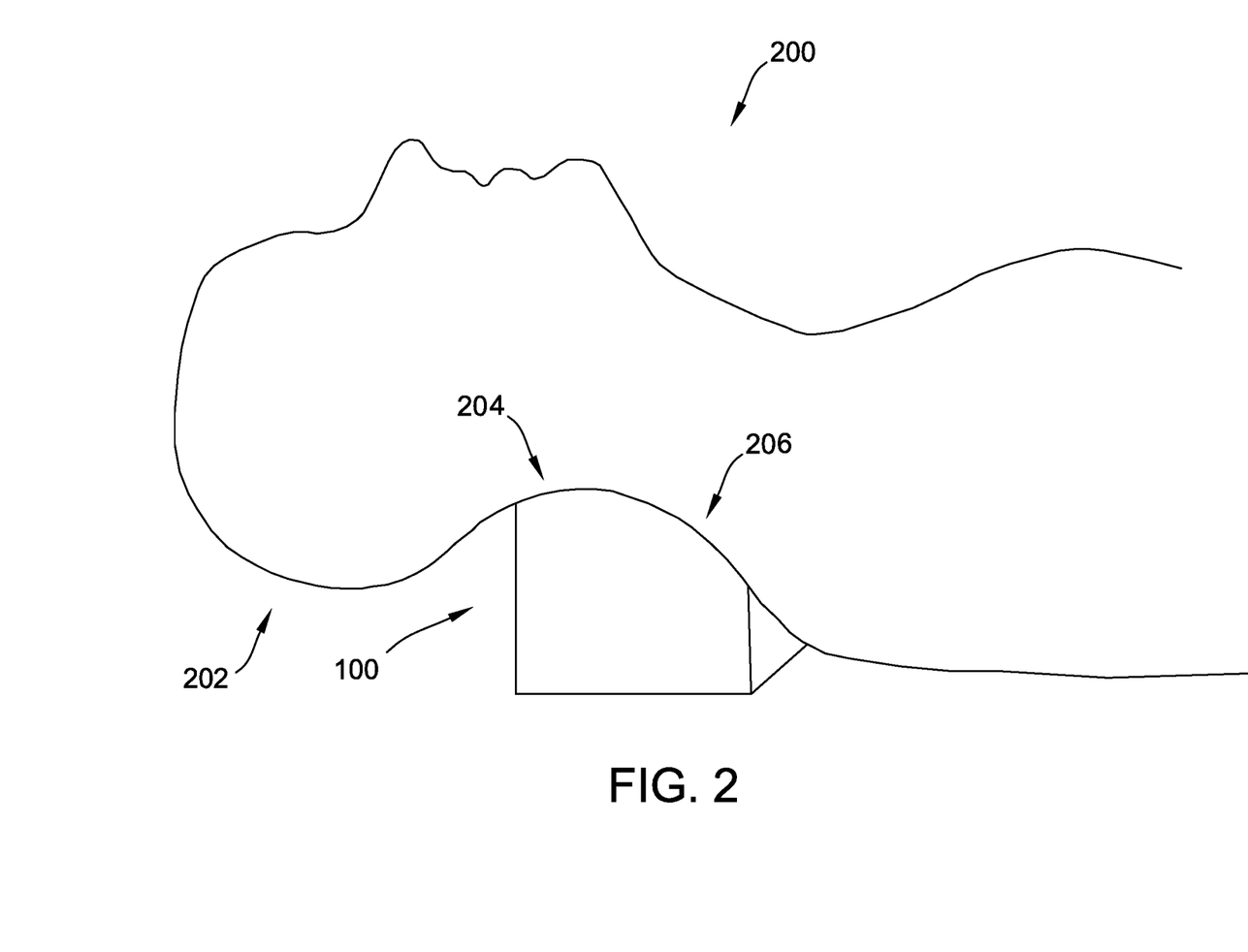
FIG. 2 illustrates a patient using the exemplary device shown in FIG. 1.

FIG. 1 is a schematic perspective view of an exemplary device 100 for delivering low-level electromagnetic radiation to one or more treatment areas of a patient. FIG. 2 illustrates an exemplary patient 200 using device 100. Device 100 includes a support 102 and a plurality of infrared emitters 104 coupled to support 102. Support 102 includes a base surface 106 and a contact surface 116. With reference to FIGS. 1 and 2, base surface 106 is substantially planar and configured to rest on a substrate (e.g., a floor). Contact surface 116 is opposite base surface 106 and contoured to support a curvature of a sub-occipital region 204 and a lower neck region 206 of patient 200 in a supine position, such that an upper portion 202 of the head of patient 200 is cantilevered beyond support 102. Infrared emitters 104 are coupled to support 102 proximate to contact surface 116. Infrared emitters 104 are configured to emit low-level electromagnetic radiation transdermally to at least one of sub-occipital region 204 and lower neck region 206.

In the exemplary embodiment, a first portion of contact surface 116, designated first contact surface 112, is contoured to support the curvature of sub-occipital region 204. More specifically, in the exemplary embodiment, first contact surface 112 is a convex surface configured to support the curvature of the base of the skull and sub-occipital region 204 of patient 200. A second portion of contact surface 116, designated second contact surface 114, is configured to support lower neck region 206 and, in the exemplary embodiment, to prevent excessive extension (or flexion) of the patient's neck. More specifically, in the exemplary embodiment, second contact surface 114 is a concave surface, such that a first distance $D_1$ extending between an apex 122 of first contact surface 112 and base surface 106 is greater than a second distance $D_2$ extending between second contact surface 114 and base surface 106. Second contact surface 114 may further extend to support the upper back and/or shoulders of patient 200. Alternatively, first contact surface 112 and second contact surface 114 each have any suitable shape that enables device 100 to function as described herein. In the exemplary embodiment, first contact surface 112 tangentially meets second contact surface 114 to support the curvature of the patient's neck, head, and shoulders.

In the exemplary embodiment, first contact surface 112 and second contact surface 114 are unitarily formed as a single continuous contact surface 116. Alternatively, first contact surface 112 and second contact surface 114 are formed separately and/or contact surface 116 is other than a single, continuous surface. In various embodiments, contact surface 116 is formed as a separable cover overlying a body of support 102, emitters 104 are embedded in the body directly beneath contact surface 116, and contact surface 116 is configured to be substantially transparent to the low-level electromagnetic radiation emitted by emitters 104. In one example, contact surface 116 is a sheet-like protective film or layer that protects emitters 104 from the environment. Correspondingly, the body of support 102 may be formed from a suitable material that enables device 100 to conform to the curvature of the patient's neck when in use, and to return to its original shape when device 100 is not being used, such as a suitable foam or cushion material that enables device 100 to compress, stretch, and conform to the curvature of a patient's neck, such that (i) the patient's neck is supported by device 100 and (ii) infrared emitters 104 are directly adjacent to the target treatment areas of the patient's neck while device 100 is in use. In alternative embodiments, a suitable form or cushion material used to form support 102 may also define contact surface 116. The suitable material may be, for example, a synthetic foam, gel, or fluid material that enables device 100 to function as described herein.

As shown in FIG. 1, base surface 106 is a substantially elongate planar surface configured to rest on a substrate surface (for example, a floor, treatment table, or bed) when device 100 is utilized by the patient. Device 100 includes side surfaces 118, 120. First side surface 118 is transversally oriented to base surface 106 and extends therefrom. Second side surface 120 is parallel to, and opposite from, first side surface 118. Second side surface 120 is transversally oriented to base surface 106 and extends therefrom. Alternatively, base surface 106 and side surfaces 118, 120 each have any suitable shape and/or orientation that enables device 100 to function as described herein.

Emitters 104 are coupled to support 102 proximate to contact surface 116 and oriented to emit energy transdermally to patient 200. In the exemplary embodiment, emitters 104 are embedded in contact surface 116, such that a patient-facing surface of each emitter 104 is flush with contact surface 116. Alternatively, emitters 104 are coupled to support 102 in any suitable fashion that enables device 100 to function as described herein. In the illustrated embodiment, emitters 104 are positioned across contact surface 116 in an arrangement that targets (i.e., that positions specific emitters 104 directly adjacent to) specific muscles in sub-occipital region 204 and lower neck region 206, such as, for example, but not limited to, the sternocleidomastoid and the trapezius muscles, when patient 200 is positioned on device 100. Device 100 may include any suitable number of emitters 104 positioned in any suitable arrangement across first contact surface 112 and second contact surface 114 for effectively administering light to the target treatment areas.

With reference to FIGS. 1 and 2, when a patient lies in a supine position with device 100 positioned underneath the patient's neck, device 100 is configured to apply a gentle stretch to the patient's neck such that target treatment areas (e.g., one or more positions of the major cervical muscles) align with one or more infrared emitters 104 of device 100 without requiring the patient to adjust placement of device 100. In the exemplary embodiment, device 100 is configured to slightly extend (e.g., stretch) the patient's neck when the patient uses device 100, such that the muscles, including the cervical muscles, are in a state of increased receptiveness to benefit from light therapy treatment. In the exemplary embodiment, emitters 104 align with target muscles in sub-occipital region 204 and lower neck region 206, in the light therapy-receptive state induced by support 102, to safely and effectively deliver near-infrared light. For example, when emitters 104 are positioned directly adjacent to the target muscles, emitters 104 increase the temperature of the muscles over a period of time, thereby promoting blood circulation to these muscles, activating metabolism, and relieving muscle tension.

In the exemplary embodiment, a first subset of emitters 104 are coupled to support 102 proximate to first contact surface 112 and are configured to emit low-level electromagnetic radiation transdermally to sub-occipital region 204, and a second subset of emitters 104 are coupled to support 102 proximate to second contact surface 114 and are configured to emit low-level electromagnetic radiation transdermally to lower neck region 206. In various embodiments, each of the first and second subsets of emitters 104 is independently activatable. Alternatively, emitters 104 are grouped and/or independently activatable in any suitable arrangement of subsets that enables device 100 to function as described herein In the exemplary embodiment, emitters 104 are operable to emit low levels of near infrared ("NIR") light. Emitters 104 may be light emitting diodes ("LEDs"), such as, for example, near-infrared LEDs. Emitters 104 may emit light continuously at a given wavelength over a predefined period of time, or alternatively may emit light in pulses at a given wavelength. The frequency, intensity, and/or wavelength of infrared emitters 104 may be fixed or may vary in accordance with signals from a controller (not shown) configured to control the operation of device 100. Emitters 104 may be configured to emit near infrared light at a wavelength within a range of about 200 nanometers (nm) to 1000 nm. In some embodiments, emitters 104 may be configured to emit near infrared light within a range of about 600-850 nm. Alternatively, emitters 104 are configured to emit near infrared light at any suitable range of wavelengths that enables device 100 to function as described herein. In some examples, at least some of the advantages described herein are achieved by emitters 104 providing energy at the above-described wavelengths, on average, in a range of about 1 milliwatt (mW) to 1,000 mW per cm$^2$. In certain examples, at least some of the advantages described herein are particularly achieved by emitters 104 providing energy at the above-described wavelengths, on average, in a range of about 5 milliwatt (mW) to 200 mW per cm$^2$. In other examples, emitters 104 are configured to provide energy at any suitable wavelength and/or energy level that enables device 100 to achieve at least some of the advantages described herein.

The controller may be in communication with emitters 104, a power source (not shown), and/or a timing mechanism (not shown) to control the frequency, wavelength, intensity, and/or duration of the light emitted by device 100. In certain embodiments, device 100 may include one or more pressure sensors (not shown) associated with first contact surface 112 and/or second contact surface 114 that enable the controller to determine which emitters 104 to automatically turn on based on the pressure detected when device 100 is in contact with the patient's neck. Additionally or alternatively, device 100 may be configured to vibrate or pulsate to gently apply pressure and massage the patient's treatment areas while light is being administered to these treatment areas.

In alternative embodiments, device 100 may include an external controller (not shown) or a user computing device (not shown), such as a mobile device (e.g., a smart phone) in communication with the controller. For example, the patient may utilize the user computing device to remotely control the settings associated with device 100. In this example, the patient may remotely adjust the duration of a light therapy session (e.g., instruct the controller to automatically turn off after a set time period and/or after a threshold temperature value is exceeded), adjust the intensity of light being delivered, and/or select one or more emitters 104 to emit light for a session. The power source (not shown) may be housed inside device 100, and may be, for example, one or more internal batteries for providing power to emitters 104. However, device 100 may include any suitable power source for providing power, such as, for example, a plug-in power cord.

Figure 3:
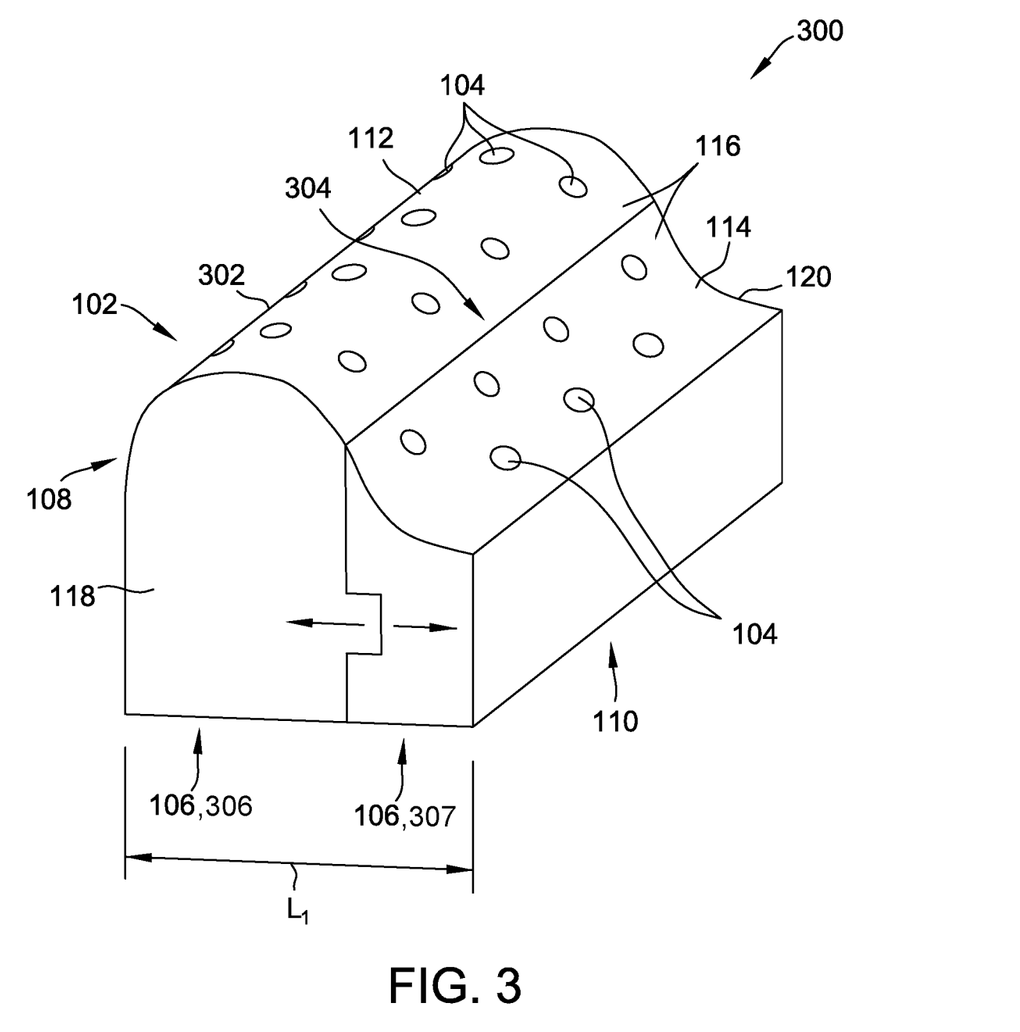
FIG. 3 is a schematic perspective view of an exemplary alternative embodiment of the device shown in FIG. 1.
Figure 4:
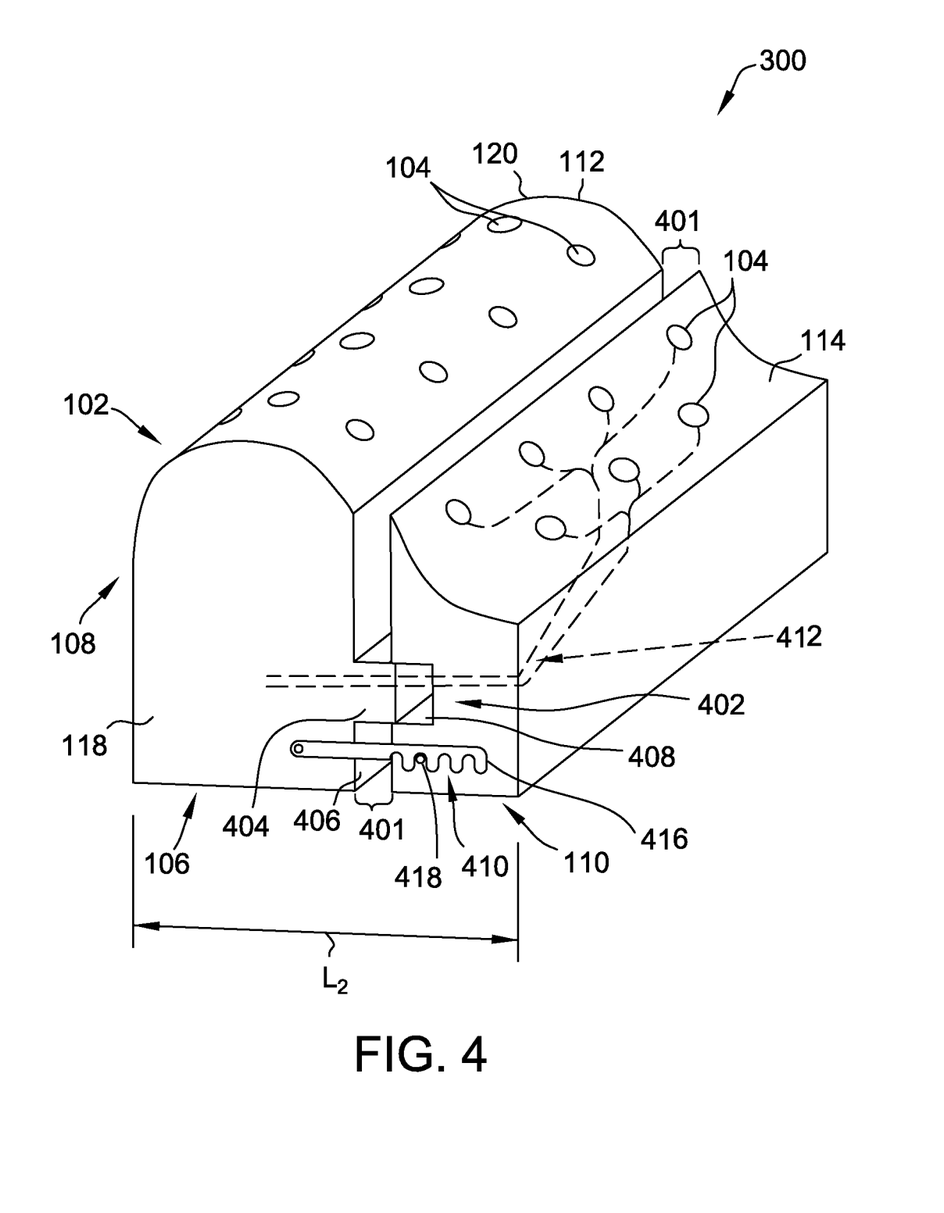
FIG. 4 is a schematic perspective view of the exemplary alternative embodiment of the device shown in FIG. 3, showing the device in an expanded configuration.

FIG. 3 is a schematic perspective view of an exemplary alternative embodiment of device 100 (shown in FIG. 1), designated device 300. FIG. 4 is a schematic perspective view of device 300 in an expanded configuration. In the exemplary embodiment, support 102 is defined by a first support element 108 and a second support element 110. First support element 108 includes a first portion 306 of base surface 106, and first contact surface 112 is opposite first portion 306 of base surface 106. Second support element 110 includes a second portion 307 of base surface 106, and second contact surface 114, and second contact surface 114 is opposite second portion 307 of base surface 106. First support element 108 and second support element 110 are movable relative to each other to adjust a spacing 401 between first contact surface 112 and second contact surface 114. In other words, device 300 is configured to expand from an original configuration having a first length $L_1$ to an expanded configuration having a second length $L_2$ to accommodate patients having different neck lengths, such as, for example, those with longer than average neck lengths. In various embodiments, patients may choose to adjust spacing 401 of device 300 to improve simultaneous alignment of emitters 104 on first contact surface 112 with sub-occipital region 204, and emitters 104 on second contact surface 114 with lower neck region 206. For example, a patient with a longer neck may expand gap 401 to simultaneously target various points of the upper and lower cervical muscles.

In the exemplary embodiment, first support element 108 and second support element 110 are configured to meet at a seam 304 extending from first side surface 118 to second side surface 120. Device 300 is configured to separate at seam 304 and transition from the original configuration to the expanded configuration, such that gap 401 is adjustably defined between first support element 108 and second support element 110. In the exemplary embodiment, seam 304 is generally planar and is generally transverse to side surfaces 118, 120 and to base surface 106. Alternatively, seam 304 has any suitable shape and/or orientation that enables device 300 to function as described herein.

In the exemplary embodiment, support elements 108, 110 are coupled together connected via a connector mechanism 402 that extends across seam 304. In the illustrated embodiment, connector mechanism 402 includes at least one protrusion 404 extending outward from an inner wall 406 of first support element 108 towards second support element 110, and second support element 110 includes at least one recess 408 registered with protrusion 404 and sized to receive protrusion 404 therein in a clearance fit. More specifically, protrusion 404 is configured to slide within recess 408 to maintain a coupling of first support element 108 and second support element 110 when support elements 108, 110 are moved relative to each other. It should be understood that protrusion 404 and recess 408 may be oppositely disposed on second support element 110 and first support element 108, respectively. Alternatively, any suitable connector mechanism 402 may be utilized to movably couple first support element 108 and second support element 110.

Further in the exemplary embodiment, device 300 includes a locking mechanism 410 configured to selectively lock a position of first support element 108 and second support element 110 at a plurality of positions relative to each other. For example, locking mechanism 410 is configured to fix first support element 108 and second support element 110 in place while device 300 is in an expanded configuration, as shown in FIG. 4. In the example embodiment, locking mechanism 410 includes a slotted arm 416 rotatably mounted on first side surface 118 of first support element 108 and a peg 418 fixed on first side surface 118 of second support element 110 and configured to be selectively received by each slot on arm 416. A similar locking mechanism 410 may be provided on second side surface 120 for added stability. Alternatively, locking mechanism 410 may be any suitable mechanism for locking first support element 108 and second support element 110 in position relative to each other, such as, for example, adjustable fasteners, tabs, and geared knobs.

In addition, in the exemplary embodiment, connector mechanism 402 includes a conduit 412 for maintaining control and/or power connections to emitters 104 when first support element 108 and second support element 110 are separated. For example, a power source (e.g., a battery) and/or a controller (not shown) may be housed in first support element 108, and conduit 412 may enable safe and efficient routing of conductive wires for power and/or control signals from first support element 108 to emitters in second support element 110.

Figure 5:
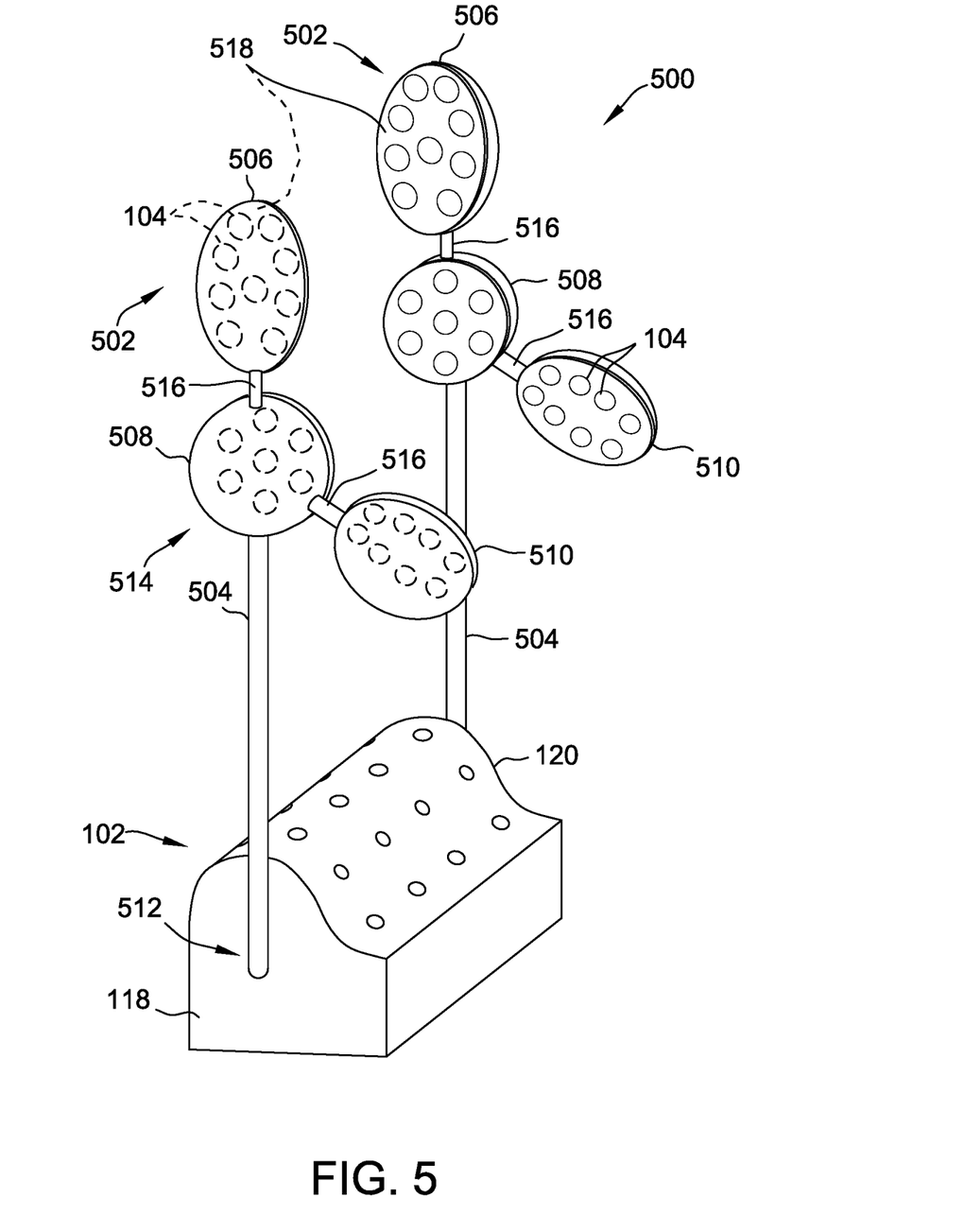
FIG. 5 is a schematic perspective view of another exemplary alternative embodiment of the device shown in FIG. 1.
Figure 6:
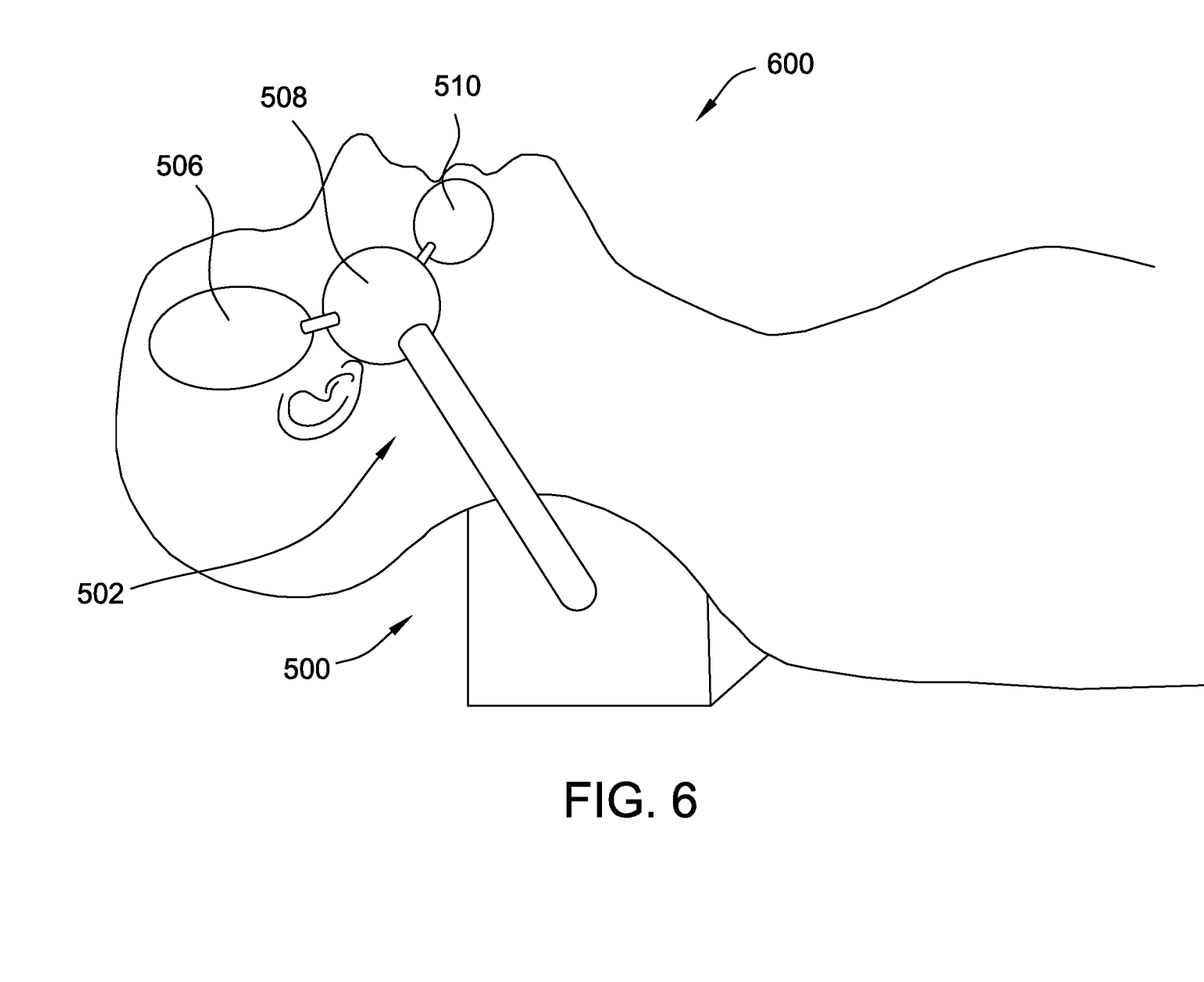
FIG. 6 is a schematic perspective view of a patient using the exemplary alternative embodiment of the device shown in FIG. 5.

FIG. 5 is a schematic perspective view of another exemplary alternative embodiment of device 100 (shown in FIG. 1), designated device 500. FIG. 6 is a schematic perspective view of a patient 600 using device 500. Device 500 is substantially identical to embodiments of device 100 as described above with respect to FIGS. 1-4, except as described below. In particular, with reference to FIGS. 5 and 6, device 500 includes at least one side arm assembly 502 coupled to support 102. In the illustrated embodiment, the at least one side arm assembly 502 includes a pair of side arm assemblies extending respectively from first side surface 118 and second side surface 120. Each side arm assembly 502 includes a support arm 504 and at least one support pad, such as one or more of support pads 506, 508, 510.

Support arm 504 includes a first end 512 and a second end 514. Each side arm assembly 502 is coupled to support 102 at first end 512 of support arm 504. In some embodiments, each side arm assembly 502 is rotatably coupled to support 102 at first end 512. In other embodiments, each side arm assembly 502 is fixed to support 102 at first end 512. In certain embodiments, each support arm 504 is configured to bend along one or more selected portions in response to manual manipulation, and maintain each resulting bended position (e.g., bended shape) such that side arm assemblies 502 may be selectively positioned toward the patient's head and face. Each support arm 504 may be formed from a flexible, repeatably bendable material that tends to retain each bended shape, such as, for example, a gooseneck tubing material made from rubber, polymer, and/or any suitable material.

Each support pad includes an inner, or patient-facing, surface 518 configured to contact a region of the face of patient 600 when support arm 504 is properly positioned. In the exemplary embodiment, the at least one support pad includes a temporal pad 506 configured to contact a temporal region of the patient's face, a TMJ pad 508 configured to contact a temporomandibular joint region of the patient's face, and a masseter pad 510 configured to contact a jaw region of the patient's face, when patient 600 is supine and supported on support 102. In alternative embodiments, the at least one support pad includes any suitable number of support pads configured to contact any suitable portion of the patient's face for light therapy treatment as described herein. Emitters 104 are embedded on inner surface 518 of each support pad 506, 508, and 510. More specifically, a first subset of emitters 104 associated with temporal pad 506 is configured to emit low-level electromagnetic radiation transdermally to the patient's temporal muscle. A second subset of emitters 104 associated with TMJ pad 508 is configured to emit low-level electromagnetic radiation transdermally to a temporomandibular joint region of the patient's face. A third subset of emitters 104 associated with masseter pad 510 is configured to emit low-level electromagnetic radiation transdermally to a jaw region of the patient (i.e., including a lower region of the masseter muscle). Each of first, second, and third subsets of emitters 104 is independently activatable.

In embodiments where the at least one support pad numbers more than one, each side arm assembly 502 also includes pad connectors 516 configured to connect the multiple pads. For example, in the illustrated embodiment, respective pad connectors 516 connect temporal pad 506 and masseter pad 510 to TMJ pad 508. Pad connectors 516 enable further positioning and orientation of support pads 506 and 510 relative to support pad 508, to facilitate better positioning and contact of the plurality of support pads on the targeted regions of the patient's face. Pad connectors 516 may include a ball and socket joint configuration at one or both ends of each pad connector 516. In alternative embodiments, pad connectors 516 are configured to bend along one or more selected portions in response to manual manipulation, and maintain each resulting bended position (e.g., bended shape) such that one or more of pads 506, 508, and 510 may be selectively positioned on the patient's face. In these embodiments, pad connectors 516 may be formed from a flexible, repeatably bendable material as described above with respect to support arm 504.

Thus, in the exemplary embodiment, device 500 enables dosages of light therapy to be administered to treatment areas of the neck via infrared emitters 104 of contact surface 116 as well as to areas of the patient's head and face via emitters 104 of support pads 506, 508, 510. This enables a patient to conveniently treat multiple areas with, for example, NIR light at the same time. In particular, it has been discovered that support 102, sized and contoured to induce the muscles and surrounding tissues in sub-occipital region 204 and lower neck region 206 into the light therapy-receptive state described above, advantageously further tends to induce the light therapy-receptive state in the temporal, TMJ, and lower masseter muscles and surrounding tissues associated with TMD. A position of each support pad 506, 508, 510 relative to support 102 is adjustable to align a second plurality of emitters 104 with these TMD-specific muscle groups and other tissues while they are in the receptive state induced by use of support 102.

Alternatively, device 500 does not include the first plurality of emitters 104 on contact surface 116, and targets light therapy solely using the at least one support pad. In various embodiments, device 500 further includes adjustable first and second support elements 108, 110 as described in FIGS. 3 and 4.

Figure 7:
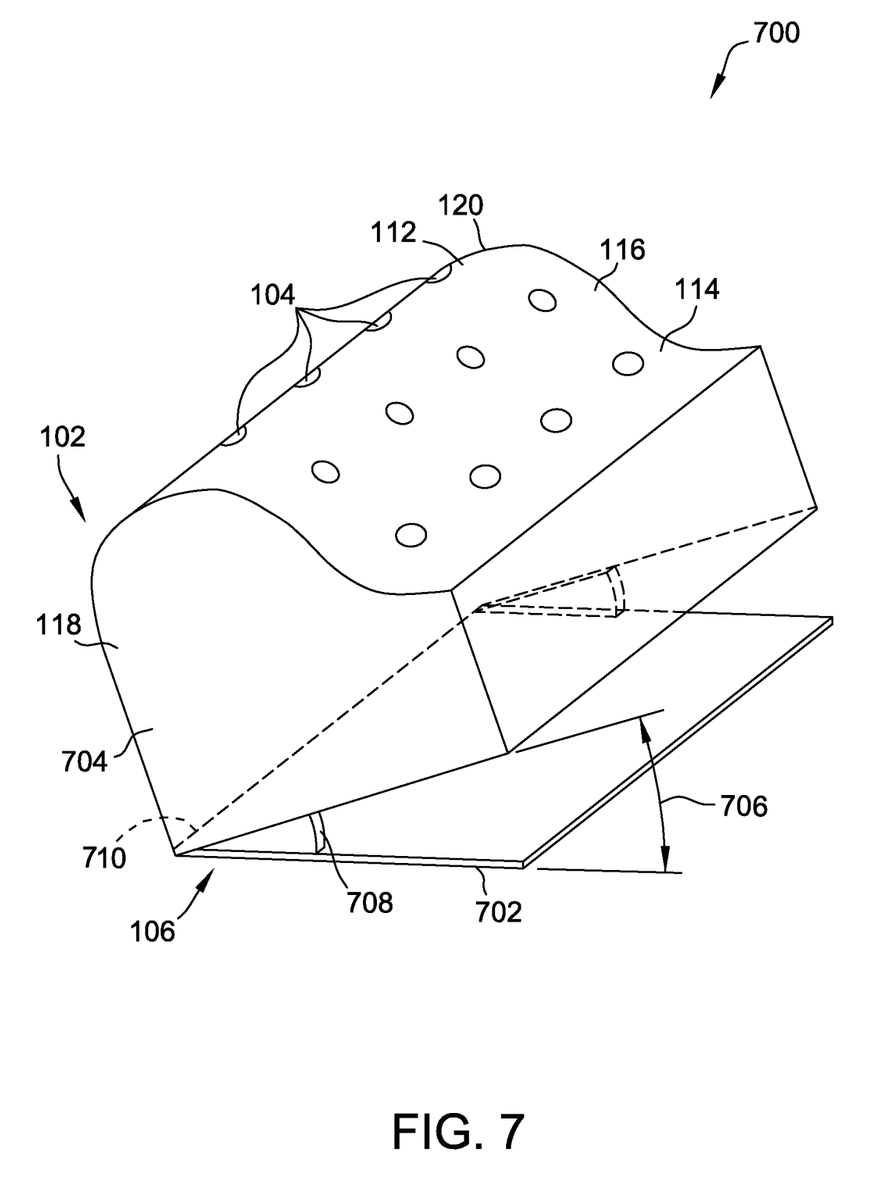
FIG. 7 is a schematic perspective view of another exemplary alternative embodiment of the device shown in FIG. 1.

FIG. 7 is a schematic perspective view of another exemplary alternative embodiment of device 100 (shown in FIG. 1), designated device 700. Device 700 is substantially identical to the embodiments of device 100 as described above with respect to FIGS. 1-6, except as described below. In particular, device 700 includes support 102, which includes base surface 106. Base surface 106 is defined by a support plate 702. A position of a remainder of support 102, designated body 704, is adjustable relative to support plate 702 to vertically adjust portions of contact surface 116, such as first contact surface 112, relative to other portions of contact surface 116, for example to accommodate physical requirements of a particular patient's head in order to achieve the desired receptive state of the target muscle groups and/or the desired alignment of emitters 104 and the target muscle groups.

In the exemplary embodiment, device 700 includes an adjustment mechanism 708, such as, for example, a stepped gear mechanism, coupled in at least one location between support plate 702 and body 704. Adjustment mechanism 708 is configured to adjust a position of body 704 relative to support plate 702. In the illustrated embodiment, adjustment mechanism is located in two corners of device 700, enabling rotational adjustment of body 704 relative to base surface 106 at an angle 706 about an axis 710 extending perpendicular to first side surface 118. Additionally or alternatively, adjustment mechanism 708 is provided in all four corners of device 700, enabling elevation of body 704 evenly with respect to support plate 702. In such embodiments, an entirety of contact surface 116 may be raised and lowered relative to base surface 106 to accommodate different physical requirements of different patients. Alternatively, device 700 includes any suitable number and locations of adjustment mechanism 708 that enables device 700 to function as described herein.

In some embodiments, adjustment mechanism 708 is manually adjusted via a mechanical connection to a knob (not shown) on one or more side surfaces of device 700, such as side surfaces 118, 120. In other embodiments, adjustment mechanism 708 is electronically adjustable by a controller, as described above.

Figure 8:
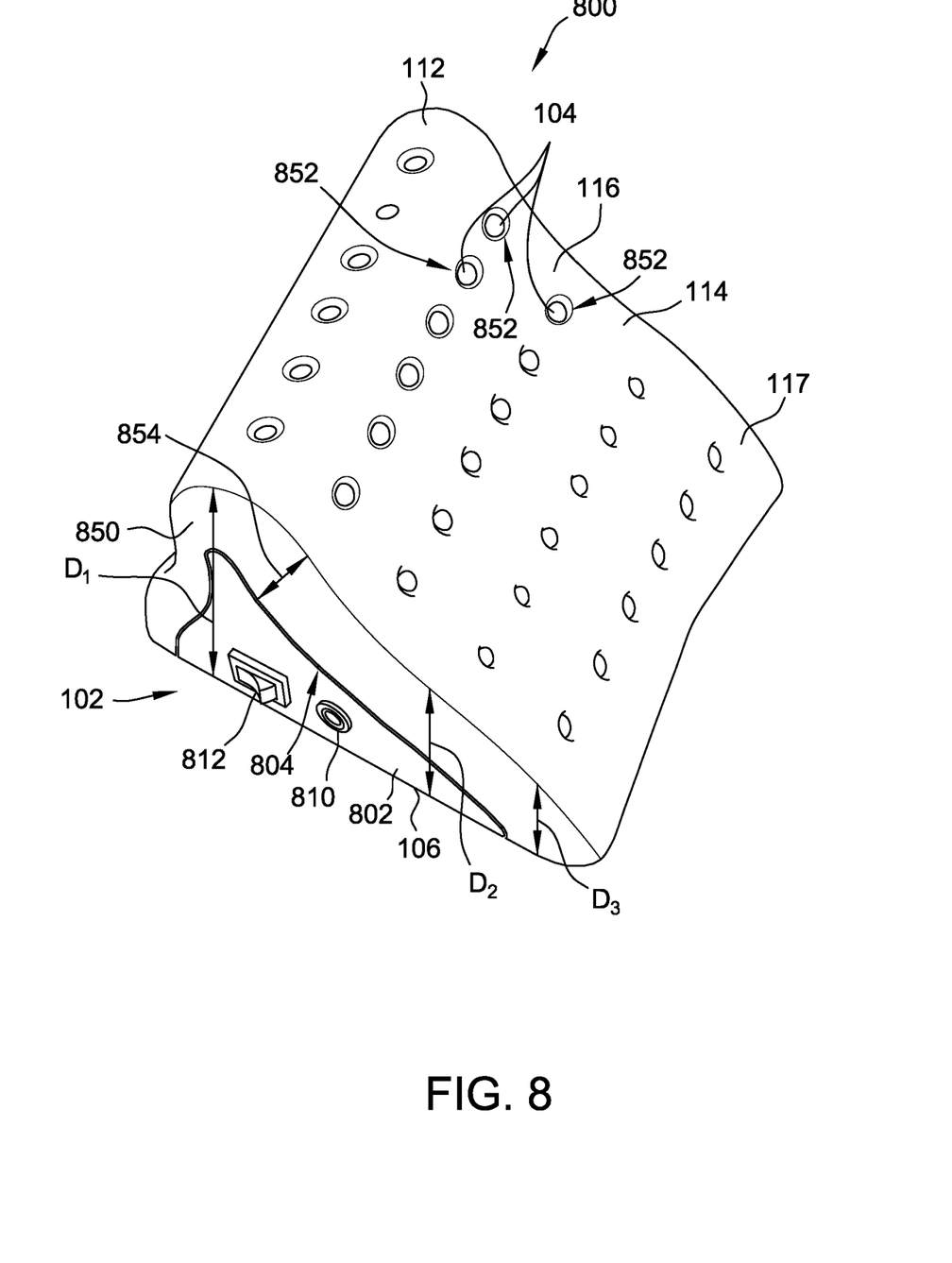
FIG. 8 is a schematic perspective view of another exemplary alternative embodiment of the device shown in FIG. 1.
Figure 9:
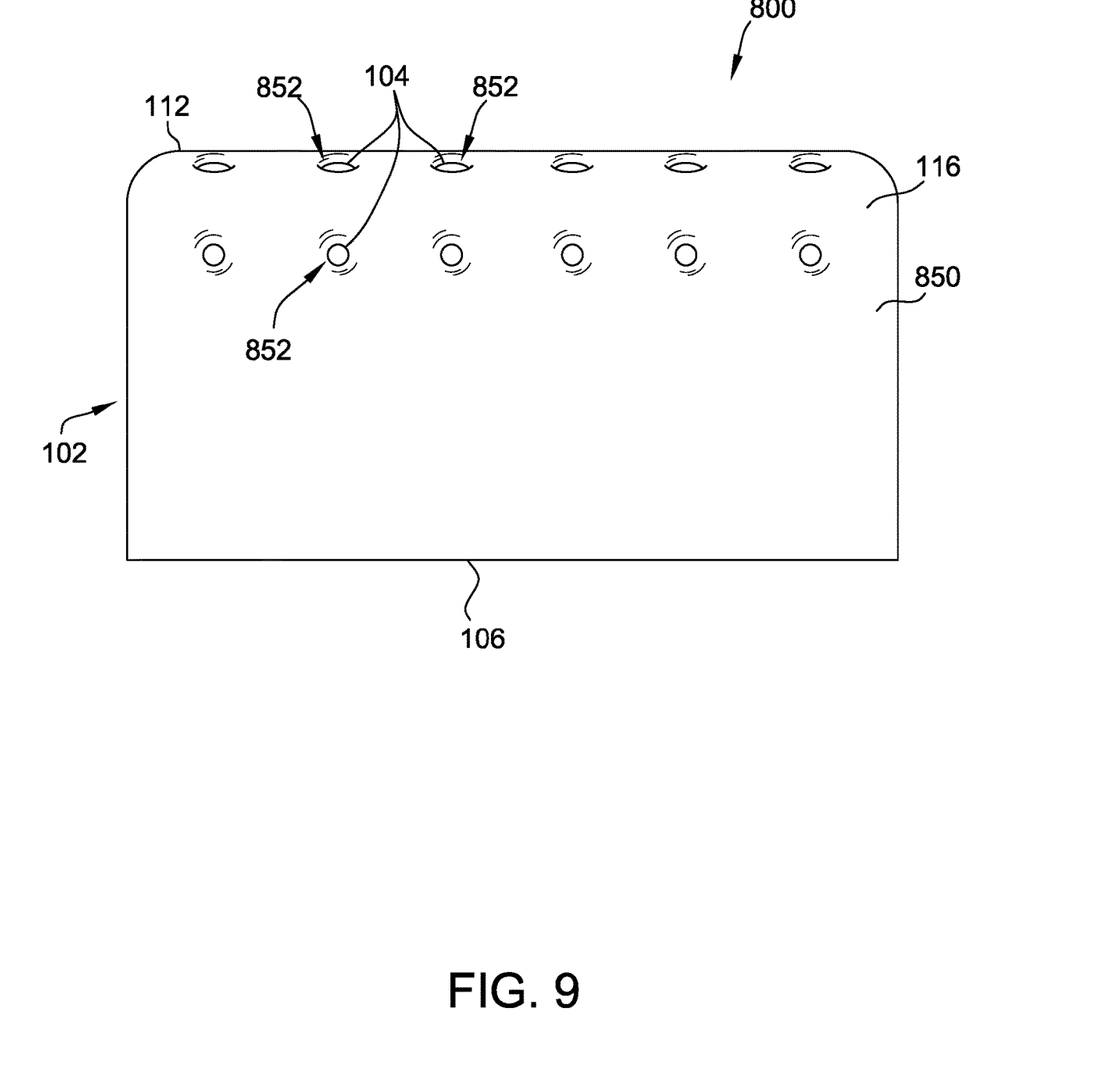
FIG. 9 is a back elevation view of the exemplary alternative embodiment of the device shown in FIG. 8.

FIG. 8 is a schematic perspective view of another exemplary alternative embodiment of device 100 (shown in FIG. 1), designated device 800. FIG. 9 is a back elevation view of device 800. Device 800 is substantially identical to the embodiments of device 100 as described above with respect to FIGS. 1 and 2, except as described below. For example, device 800 again includes support 102, which again includes base surface 106, contact surface 116 opposite base surface 106 and contoured to support a curvature of a sub-occipital region 204 and a lower neck region 206 of patient 200 in a supine position such that an upper portion of the head of patient 200 is cantilevered beyond support 102, and infrared emitters 104 coupled to support 102 proximate to contact surface 116. Contact surface 116 again includes first contact surface 112, contoured to support the curvature of sub-occipital region 204, and second contact surface 114, configured to support lower neck region 206. More specifically, in the exemplary embodiment, second contact surface 114 is again a concave surface, and first contact surface 112 is again a convex surface having an apex extending to a first distance $D_1$ from base surface 106 that is greater than a second distance $D_2$ extending between second contact surface 114 and base surface 106.

In some embodiments, device 800 again includes a first subset of emitters configured to emit low-level electromagnetic radiation transdermally to the sub-occipital region, and a second subset of emitters configured to emit low-level electromagnetic radiation transdermally to the lower neck region. For example, as shown in FIG. 9, the first subset of emitters 104 includes emitters 104 arranged on a back-facing side of first contact surface 112 and oriented to emit energy transdermally to the sub-occipital region of patient 200.

In addition, in the exemplary embodiment, contact surface 116 of device 800 includes a third portion, designated third contact surface 117, that is contoured to support the curvature of the upper back and/or shoulders of patient 200. More specifically, in the exemplary embodiment, third contact surface 117 is a convex surface that extends in a smooth transition from second contact surface 116, such that second contact surface 116 is located between first contact surface 112 and third contact surface 117. Third contact surface 117 extends to a third distance $D_3$ from base surface 106 that is less than second distance $D_2$. In some embodiments, third contact surface provides enhanced support for the upper back and/or shoulders of patient 200, and further cooperates with first and second contact surfaces 112 and 114 to gently stretch the patient's sub-occipital muscles, as well as surrounding tissues and muscle groups in the lower neck and head, into the light therapy-receptive state described above. Alternatively, first contact surface 112, second contact surface 114, and third contact surface 117 each have any suitable shape that enables device 100 to function as described herein. In the exemplary embodiment, a third subset of emitters 104 is arranged on third contact surface 117 to emit low-level magnetic radiation to the upper back and/or shoulders. Alternatively, no emitters 104 are arranged on third contact surface 117.

In some embodiments, support 102 includes a core portion 802 and a cushion layer 850. More specifically, core portion 802 defines at least a portion of base surface 106 and includes an upper surface 804 opposite base surface 106. Cushion layer 850 substantially defines contact surface 116 and is mounted on upper surface 804 of core portion 802.

In some such embodiments, core portion 802 is formed from a substantially rigid material, such as a hard plastic, and securely houses electronic components therewithin such as a controller (not shown), a rechargeable battery (not shown), and/or other components associated with control, power supply, and operation of emitters 104. In addition, core portion 802 includes control and input hardware arranged for easy access by a user, such as a connector 810 for a power cord for powering emitters 104 and/or recharging the internal battery, and an on/off switch 812. Additionally or alternatively, core portion 802 includes any other suitable control and/or input hardware.

Moreover, in some such embodiments, cushion layer 850 is formed from a suitable foam or cushion material that compresses and conforms to the curvature of the patient's neck, such that (i) the patient's neck is comfortably supported by device 100 and (ii) infrared emitters 104 are directly adjacent to the target treatment areas of the patient's neck while device 100 is in use. In certain embodiments, this structural separation of the rigid core portion 802 and the relatively soft/flexible cushion layer 850 enables device 100 to provide the comfort and/or therapy advantages described above while protecting associated electronic components within a structurally sound housing. Alternatively, each of core portion 802 and cushion layer 850 is formed form any suitable material that enables device 100 to function as described herein.

In the exemplary embodiment, upper surface 804 defines a contour substantially similar to a contour of contact surface 116, and cushion layer 850 is formed from a layer of foam or cushion material of a substantially constant (excepting apertures 852, as discussed below) thickness 854 form-fitted against upper surface 804. For example, core portion 802, including upper surface 804, is formed in a plastic molding process. In some such embodiments, this construction enables an ease of, and reduces a cost of, manufacture of device 100. Alternatively, upper surface 804 has any suitable shape and/or cushion layer 850 is formed in any suitable fashion that enables device 100 to function as described herein.

As discussed above, emitters 104 are coupled to support 102 proximate to contact surface 116 and oriented to emit energy transdermally to patient 200. In certain embodiments, this is implemented by emitters 104 affixed to upper surface 804 of core portion 802, and apertures 852 defined in cushion layer 850 and arranged to register with emitters 104. More specifically, emitters 104 are affixed to upper surface 804 and oriented to emit energy transdermally to patient 200 via apertures 852. In the exemplary embodiment, apertures 852 extend entirely through a thickness 854 of cushion layer 850. Alternatively, apertures 852 extend less than entirely through thickness 854, such that a relatively thin layer of material of cushion layer 850 is disposed over emitters 104 and is substantially transparent to the low-level electromagnetic radiation emitted by emitters 104.

Alternatively, emitters 104 are coupled to support 102 proximate to contact surface 116 in any suitable fashion that enables device 100 to function as described herein.

Figure 10:
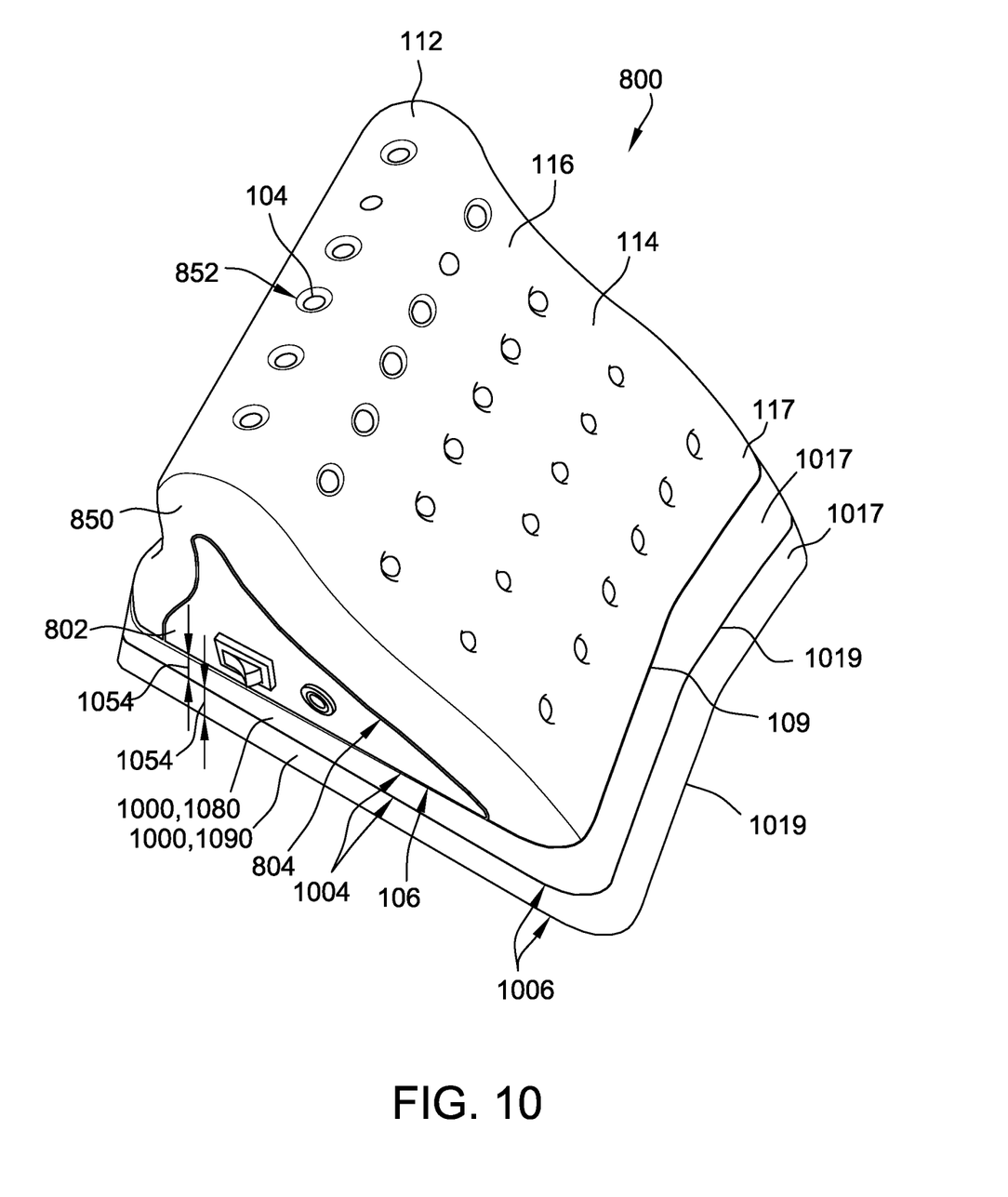
FIG. 10 is a schematic perspective view of the exemplary alternative embodiment of the device shown in FIG. 8, including exemplary elevator platforms.

FIG. 10 is a schematic perspective view of device 800, including exemplary elevator platforms 1000 coupled underneath base surface 106. Elevator platforms 1000 are configured for selective coupling underneath base surface 106 to adjust an elevation of contact surface 116 relative to a substrate (for example, a floor, treatment table, or bed) on which device 100 rests, for example to accommodate physical requirements of a particular patient's head in order to achieve the desired receptive state of the target muscle groups and/or the desired alignment of emitters 104 and the target muscle groups.

More specifically, in the exemplary embodiment, each elevator platform extends from an elevator base surface 1006 to an elevator upper surface 1004 over an elevator thickness 1054. In the exemplary embodiment, elevator upper surface 1004 of a first elevator platform 1080 is configured to couple against base surface 106 of support 106, and elevator base surface 1006 of first elevator platform 1080 is configured to rest on the substrate, thereby elevating contact surface 116 by thickness 1054 relative to configurations in which base surface 106 rests directly on the substrate.

In some embodiments, a plurality of elevator platforms 1000 are configured for sequential stacking underneath base surface 106, for example to accommodate patients who need a larger adjustment of the elevation of contact surface 116. More specifically, in the exemplary embodiment, elevator upper surface 1004 of a second elevator platform 1090 is configured to couple against elevator base surface 1006 of first elevator platform 1080, and elevator base surface 1006 of second elevator platform 1090 is configured to rest on the substrate, thereby elevating contact surface 116 by thickness 1054 of first elevator platform 1080 plus thickness 1054 of second elevator platform 1090 relative to configurations in which base surface 106 rests directly on the substrate. In some embodiments, thickness 1054 of first elevator platform 1080 is substantially equal to thickness 1054 of second elevator platform 1090. Alternatively, thickness 1054 of first elevator platform 1080 differs substantially from thickness 1054 of second elevator platform 1090.

Elevator platforms 1000 are suitably configured for ease of coupling, and decoupling from, underneath base surface 106. For example, but not by way of limitation, elevator upper surface 1004 of first elevator platform 1080 is configured to snap fit into base surface 106 of support 106, and elevator upper surface 1004 of second elevator platform 1090 is configured to snap fit into elevator base surface 1006 of first elevator platform 1080. Alternatively, elevator platforms 1000 are configured for coupling to and decoupling from underneath base surface 106 in any suitable fashion that enables elevator platforms 1000 to function as described herein.

Although two elevator platforms 1000 are illustrated in FIG. 10, it should be understood that any suitable number of elevator platforms 1000 may be provided and configured for sequential stacking underneath base surface 106 of support 102 to enable a corresponding adjustment of the elevation of contact surface 116 relative to the substrate. in certain embodiments, providing a plurality of stackable elevator platforms 1000 enables a single device 100 to be effectively used by multiple patients (e.g., family members) having different physical requirements, eliminating a need to obtain a differently sized device 100 for each user.

In some embodiments, as an alternative or addition to stacking elevator platforms 1000 to provide different adjustments to the elevation of contact surface 116, a set of first elevator platforms 1000 each having a different thickness 1054 may be provided for selective, one-at-a-time use with support 102 in order to provide different elevations of contact surface 116 relative to the substrate.

In the exemplary embodiment, each elevator platform 1000 is formed from a rigid plastic material. Alternatively, each elevator platform 1000 is formed from any suitable material that enables device 100 to function as described herein.

In the exemplary embodiment, each elevator platform 1000 is shaped as a generally flat plate having elevator upper surface 1004 congruent to the base surface to which it is intended to couple. For example, elevator upper surface 1004 of first elevator platform 1080 is congruent to base surface 106, elevator upper surface 1004 of second elevator platform 1090 is congruent to elevator base surface 1006 of first elevator platform 1080, etc. In other embodiments, each elevator platform 1000 is shaped as a frame having elevator upper surface 1004 configured to extend around and underneath a perimeter of the base surface to which it is intended to couple. Alternatively, each elevator platform 1000 has any suitable shape that enables device 100 to function as described herein.

In the exemplary embodiment, each elevator platform 1000 includes a platform contact surface 1017 contoured to extend generally forward from a front edge 109 of base surface 106. For example, platform contact surface 1017 of first elevator platform 1080 slopes downward and forward from front edge 109 of base surface 106 to a platform front edge 1019 of first elevator platform 1080, platform contact surface 1017 of second elevator platform 1090 slopes downward and forward from platform front edge 1019 of first elevator platform 1080 to platform front edge 1019 of second elevator platform 1090, etc. Further in the exemplary embodiment, platform contact surface 1017 of each elevator platform 1000 is shaped to cooperate with a curvature of contact surface 116 to form a substantially smooth, continuous contour that enhances a comfort of patient 200. For example, platform contact surface 1017 of first elevator platform 1080 is shaped to match a curvature of third contact surface 117 along front edge 109, and extend that curvature smoothly across platform contact surface 1017, and platform contact surface 1017 of second elevator platform 1090 is shaped to match a curvature of platform contact surface 1017 of first elevator platform 1080 along platform front edge 1019, and extend that curvature smoothly across platform contact surface 1017. Alternatively, platform contact surface 1017 of each elevator platform 1000 has any suitable shape that enables device 100 to function as described herein, or elevator platform 1000 does not include platform contact surface 1017 extending forward from front edge 109 of base surface 106.

Although not illustrated in FIGS. 8-10, embodiments including the specific features illustrated for device 800 may further include the at least one side arm assembly 502 (shown in FIGS. 5 and 6) coupled to support 102, as described above.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

This written description uses examples to illustrate the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A device for delivering low-level electromagnetic radiation to a patient, said device comprising:
  a core portion comprising an upper surface and defining at least a portion of a base surface opposite said upper surface, wherein said base surface is planar and configured to rest on a substrate;
  a cushion layer mounted on said upper surface and defining a contact surface, wherein said contact surface is opposite said base surface and contoured to support a curvature of a sub-occipital region and a lower neck region of the patient in a supine position; and
  a plurality of emitters affixed to said upper surface of said core portion and aligned with a corresponding plurality of apertures defined in said cushion layer, said plurality of emitters being configured to emit low-level electromagnetic radiation through the plurality of apertures in said cushion layer and transdermally to at least one of the sub-occipital region and the lower neck region, wherein said plurality of emitters comprises:
- a first subset of emitters positioned on said core portion to emit low-level electromagnetic radiation transdermally to the sub-occipital region; and
- a second subset of emitters positioned on said core portion to emit low-level electromagnetic radiation transdermally to the lower neck region while the first subset of emitters emit low-level electromagnetic radiation transdermally to the sub-occipital region.

2. The device according to claim 1, wherein said core portion is formed from a rigid material and said cushion layer is formed from a material that is compressible and conformable to a curvature of a neck of the patient.

3. The device according to claim 1, wherein said upper surface defines a contour similar to a contour of said contact surface, and said cushion layer comprises a layer of constant thickness form-fitted against said upper surface.

4. The device according to claim 1, wherein said apertures extend entirely through a thickness of said cushion layer.

5. The device according to claim 1, wherein said apertures extend less than entirely through a thickness of said cushion layer, such that a relatively thin layer of a material of cushion layer is disposed over said emitters and is transparent to the low-level electromagnetic radiation emitted by said emitters.

6. The device according to claim 1, wherein said plurality of emitters comprises a third subset of emitters positioned on said core portion to emit low-level electromagnetic radiation transdermally to at least one of an upper back and shoulders of the patient.

7. The device according to claim 1, wherein said plurality of emitters is configured to emit near infrared light.

8. The device according to claim 1, further comprising at least one elevator platform coupled underneath said base surface, said at least one elevator platform configured for selective coupling underneath said base surface to adjust an elevation of said contact surface relative to the substrate.

9. The device according to claim 8, wherein said at least one elevator platform comprises a plurality of elevator platforms configured for sequential stacking underneath said base surface.

10. The device according to claim 9, wherein said plurality of elevator platforms comprises a first elevator platform and a second elevator platform, each of said elevator platforms extending from an elevator base surface to an elevator upper surface over an elevator thickness, wherein said elevator upper surface of said first elevator platform is coupled against said base surface, and wherein said elevator upper surface of said second elevator platform is coupled against said elevator base surface of said first elevator platform.

11. The device according to claim 8, wherein said at least one elevator platform is coupled underneath said base surface via a snap fit.

12. The device according to claim 8, wherein said base surface comprises a front edge, and said at least one elevator platform comprises a platform contact surface contoured to extend generally forward from said front edge.

13. The device according to claim 12, wherein said platform contact surface slopes downward and forward from said front edge.

14. The device according to claim 13, wherein said platform contact surface is shaped to cooperate with a curvature of said contact surface to form a smooth, continuous contour.

15. A device for delivering low-level electromagnetic radiation to a patient, said device comprising:
- a core portion comprising an upper surface and defining at least a portion of a base surface opposite said upper surface, wherein said base surface is planar and configured to rest on a substrate;
- a cushion layer mounted on said upper surface and defining a contact surface, wherein said contact surface is opposite said base surface and contoured to support a curvature of a sub-occipital region and a lower neck region of the patient in a supine position; and
- a plurality of emitters affixed to said upper surface of said core portion and aligned with a corresponding plurality of apertures defined in said cushion layer, said plurality of emitters being configured to emit low-level electromagnetic radiation through the plurality of apertures in said cushion layer and transdermally to at least one of the sub-occipital region and the lower neck region, wherein said contact surface comprises:
  - a first contact surface contoured to support the curvature of the sub-occipital region, wherein said first contact surface comprises a convex surface; and
  - a second contact surface configured to support the lower neck region, wherein said second contact surface comprises a concave surface,
  - wherein said plurality of emitters comprises a first subset of emitters positioned on said core portion to emit low-level electromagnetic radiation from said first contact surface and a second subset of emitters positioned on said core portion to emit low-level electromagnetic radiation from said second contact surface.

16. The device according to claim 15, wherein said contact surface further comprises a third contact surface contoured to support a curvature of at least one of an upper back and shoulders of the patient, wherein said plurality of emitters further comprises a third subset of emitters positioned on said core portion to emit low-level electromagnetic radiation from said third contact surface.

17. The device according to claim 16, wherein said third contact surface comprises a convex surface.

18. The device according to claim 16, wherein said second contact surface is located between said first contact surface and said third contact surface.

* * * * *